US00PP27332P3

(12) United States Plant Patent
Olesen et al.

(10) Patent No.: US PP27,332 P3
(45) Date of Patent: Nov. 1, 2016

(54) ***CLEMATIS* PLANT NAMED 'EVIPO061'**

(50) Latin Name: *Clematis viticella*
Varietal Denomination: Evipo061

(71) Applicants: Mogens Nyegaard Olesen, Fredensborg (DK); Raymond J. Evison, St. Sampsons (GB)

(72) Inventors: Mogens Nyegaard Olesen, Fredensborg (DK); Raymond J. Evison, St. Sampsons (GB)

(73) Assignee: POULSEN ROSER A/S, Fredensborg (DK)

( * ) Notice: Subject to any disclaimer, the term of this patent is extended or adjusted under 35 U.S.C. 154(b) by 131 days.

(21) Appl. No.: 14/121,278

(22) Filed: Aug. 15, 2014

(65) Prior Publication Data

US 2016/0050829 P1 Feb. 18, 2016

(51) Int. Cl.
*A01H 5/02* (2006.01)

(52) U.S. Cl.
USPC ..... Plt./228

(58) Field of Classification Search
USPC ..... Plt./228
See application file for complete search history.

(56) References Cited

PUBLICATIONS

Perfection by Poulsen-*Clematis*—Main Varieties, 2013 (3 pgs totoal).*

* cited by examiner

*Primary Examiner* — Susan McCormick Ewoldt

(57) ABSTRACT

A new *Clematis* plant with a compact growth habit, profuse, Violet flowers, and continuous summer flowering. The variety successfully propagates from softwood cuttings and is suitable for cultivation commercial nursery culture. This new and distinct variety has shown to be uniform and stable in the resulting generations from asexual propagation from vegetative cuttings.

1 Drawing Sheet

Botanical classification: Genus: *Clematis*. Species: *viticella*.

Variety denomination: 'Evipo061'.

SUMMARY OF THE CLAIMED PLANT

The present invention constitutes a new and distinct variety of *Clematis* plant which originated from a controlled crossing between the female seed parent, an un-named, non-patented, seedling, and the male pollen parent, an un-named, non-patented, seedling.

The two parents were crossed during the summer of 2003 and the resulting seeds were planted the following winter in a controlled environment in Guernsey, Channel Islands, United Kingdom. The new variety named 'Evipo061' originated as a single seedling from the stated cross.

The new *clematis* plant may be distinguished from its female seed parent and male pollen parent by the following characteristics. The female seed parent has white anthers, while the claimed plant has violet-blue anthers. The male pollen parent has flowers which are violet-blue, while the claimed plant has flowers which are violet in color.

The objective of the hybridization of this *clematis* plant was to create a new and distinct variety for nursery culture with unique qualities such as:

1. Uniform and abundant Violet flowers;
2. Vigorous and compact growth, making the variety suitable for container culture; and
3. Improved disease resistance.

This combination of qualities was lacking in *clematis* plants that were in commercial cultivation and the qualities have been substantially achieved in the new variety.

'Evipo061' was selected by Mogens N. Olesen and Raymond J. Evison in their *clematis* development program in the Channel Islands, United Kingdom in 2004. Asexual reproduction of 'Evipo061' by means of vegetative cuttings and traditional layering was first performed by Mogens N. Olesen and Raymond J. Evison in the nursery during the summer of 2004. This initial and subsequent asexual propagations have demonstrated that the characteristics of 'Evipo061' are true to type and are transmitted from one generation to the next.

BRIEF DESCRIPTION OF THE DRAWING

The accompanying color illustration shows as true as is reasonably possible to obtain in color photographs of this type the typical characteristics of the buds, flowers, leaves, and stems, of 'Evipo061'.

Specifically illustrated in the drawing are flowers at various stages of development, flower in parts, leaves, and stems. Illustrated plants are 2 years of age.

DETAILED DESCRIPTION OF THE VARIETY

The following is a detailed description of 'Evipo061', as observed in its growth throughout the flowering period in open air cultivation in Yamhill county Oreg. Observed plants were cultivated for a period of 18 months in 2 gallon containers. Certain phenotypical characteristics of the variety may vary under different environmental, cultural, agronomic, seasonal, and climatic conditions. Color references are made using The Royal Horticultural Society (London, England) Colour Chart, 2001, except where common terms of color are used.

For a comparison, several physical characteristics of the *clematis* variety 'Evipo023' described and illustrated in U.S. Plant Pat. No. 15,166 issued Sep. 21, 2004 are compared to 'Evipo061' in Chart 1.

CHART 1

| | 'Evipo061' | 'Evipo023' |
|---|---|---|
| General tonality of flower color | Violet Group 85B with a central bar of Violet Group 84C | Violet-Blue Group 91A |
| Anther color | Violet-Blue Group N92A | Yellow 2D |

Flower and Flower Bud

Blooming habit: Recurrent. The natural flowering period is generally from May to September.

Flower bud:
- *Size*.—Normally 35 mm in length. Bud diameter is 14 mm.
- *Bud form*.—Elliptic.
- *Bud color*.—Yellow-Green Group 145A.
- *Texture*.—Lightly pubescent.

Peduncle:
- *Surface texture*.—Smooth.
- *Dimensions*.—On average 40 mm long, 2 mm wide.
- *Color*.—Yellow-Green Group 145A.
- *Strength*.—Moderately strong.

Receptacle:
- *Surface texture*.—Smooth.
- *Shape*.—Funnel.
- *Size*.—2 mm (h)×2 mm (w).
- *Color*.—Yellow-Green Group 145A.

Flower arrangement:
- *Location on vine*.—New and old growth.
- *Borne*.—Singly and in clusters of 3 per flowering branch.
- *Aspect*.—Flowers are oriented upwards and to 45 degree angle.
- *Overlapping*.—Strong.

Flower bloom:
- *Size*.—On average, flowers are 111 mm in diameter and 20 mm in depth.
- *Profile*.—Flat.
- *Fragrance*.—None.
- *Lasting quality*.—Flowers normally remain 6 days on the plant.

Tepals:
- *Tepal color*.—The upper surface is Violet Group 85B with a central bar of Violet Group 84C. The lower surface is Violet Group 85B with a central bar of Yellow-Green Group 145D.
- *Quantity*.—Normally 7 tepals.
- *Size*.—50 mm in length by 35 mm wide.
- *Shape*.—Individual tepal shape is elliptic. The tepal apex is mucronate. The tepal base is typically acute.
- *Apex recurvature*.—Recurved strongly.
- *Tepal cross section*.—Reflexed strongly.
- *Margins*.—Entire. Moderately undulated.
- *Persistence*.—Tepals drop off cleanly.

Reproductive organs:
- *Arrangement*.—Open.
- *Pollen*.—None observed.
- *Anthers*.—Size: 5 mm in length. Color: Violet-Blue Group N92A. Quantity: On average, 65.
- *Filaments*.—Color: White Group 155C. Length: 8 mm.
- *Pistils*.—Quantity: On average, 15.
- *Stigmas*.—Level in location relative to the length of the filaments and the height of the anthers.
- *Styles*.—Color: Green-White Group 157A. Length: 7 mm.

Plant

Plant form: Climbing.

Plant growth: Moderately vigorous.

Size: Seasons growth attains 3 meters in height. Average spread is 50 cm.

Stems:
- *Color*.—Juvenile stems are Yellow-Green Group 144A. Mature stems are Yellow-Green Group 144A with intonations of Greyed-Purple Group 183A.
- *Internodes*.—On average, 6 cm between nodes.
- *Length*.—Normally 40 cm from the base of the plant to the flowering portion of the stem.
- *Diameter*.—Normally 3 mm.
- *Texture*.—Mature stems ribbed.

Plant foliage:
- *Leaf characteristics*.—Deciduous.
- *Arrangement*.—Trifoliate, opposite.
- *Leaf size*.—Compound leaves are normally 80 mm (l)×85 mm (w). Leaflets are normally 45 mm (l)×25 mm (w).
- *Abundance*.—On average 4 leaves per 10 cm of stem.
- *Leaf color*.—Juvenile upper Yellow-Green Group 144A. Juvenile lower Yellow-Green Group 144A. Mature upper Yellow-Green Group 146A. Mature lower Yellow-Green Group 146B.
- *Stipules*.—Absent.
- *Petioles*.—Size: Normally 30 mm in length by 1 mm diameter. Texture: Smooth. Color: Yellow-Green Group 144A with intonations of Greyed-Orange Group 177B.
- *Petiolule*.—Size: Normally 10 mm in length by 1 mm diameter. Texture: Smooth. Color: Yellow-Green Group 144A.
- *Leaflet shape*.—Generally elliptic. The base is rounded. The apex is acute.
- *Margin*.—Entire. Some leaflets are tri-lobed.
- *Surface*.—The upper and lower surfaces are smooth.
- *Thickness*.—Moderate.
- *Glossiness*.—Matte appearance.

Disease resistance: Subject to any disease that normally attacks the species. However the variety is more tolerant to *clematis* wilt, *Phoma clematidina*, than some *clematis*.

Cold hardiness: The variety is tolerant to USDA Hardiness Zone 6.

Heat tolerance: The variety has been found to be suitable for climate conditions found in the American Horticulture Society heat zone 7.

We claim:

1. A new and distinct variety of *clematis* plant named 'Evipo061', substantially as described and illustrated, due to its abundant Violet flowers with good keepability, attractive long lasting foliage and compact growth, year round flowering under glasshouse conditions, suitability for production from softwood cuttings in pots, durable flowers and foliage which make the variety suitable for distribution in the floral industry.

* * * * *

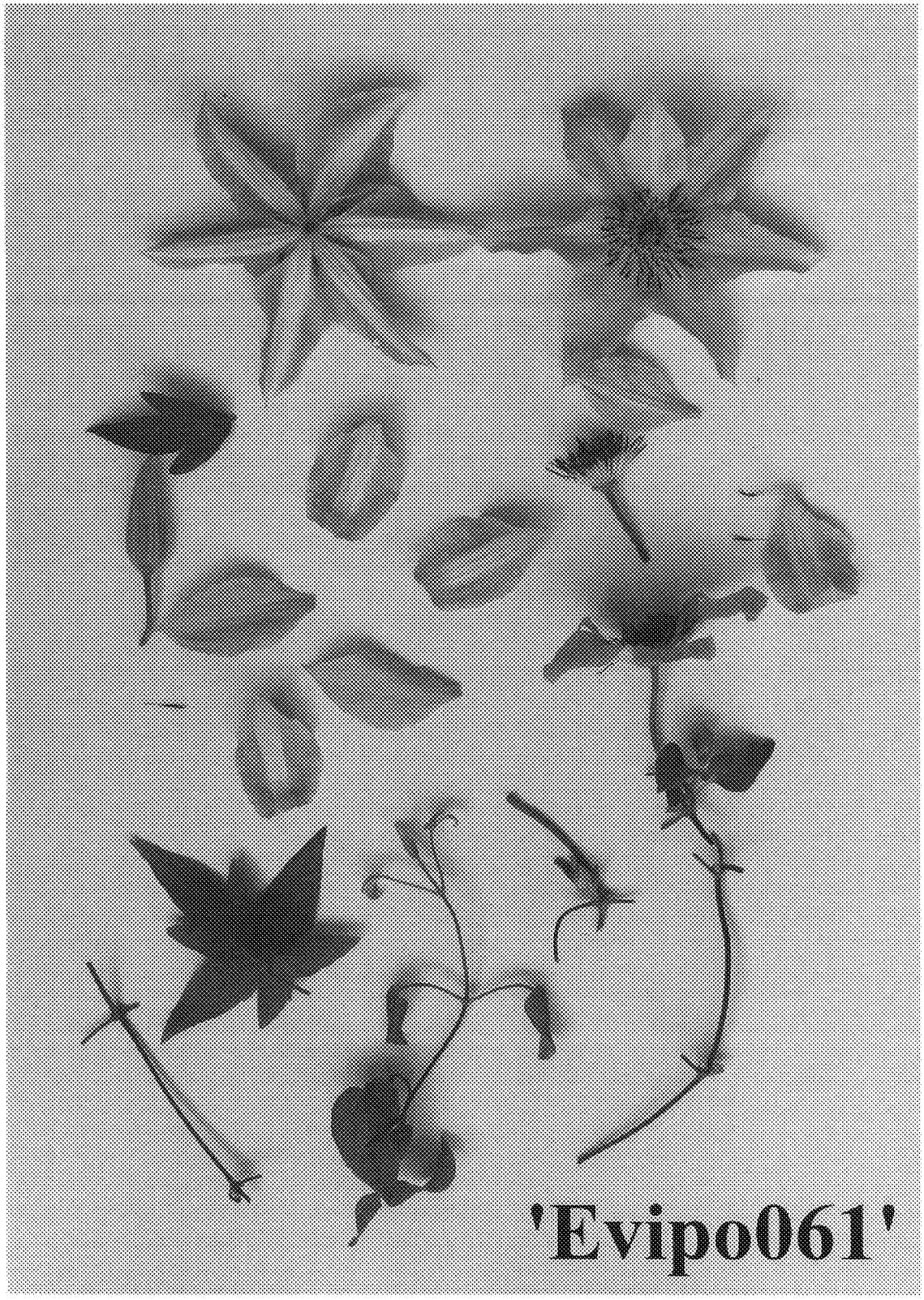
'Evipo061'